(12) United States Patent
Morrissy et al.

(10) Patent No.: US 6,783,417 B2
(45) Date of Patent: Aug. 31, 2004

(54) DISPLAY DEVICE FORMED OF A MULTI-COLOR LIGHT EMITTING MATERIAL AND METHOD OF MAKING SAME

(75) Inventors: Joseph Hourigan Morrissy, Phoenix, AZ (US); Dan Jerry Schott, Phoenix, AZ (US)

(73) Assignee: Three-Five Systems, Inc., Tempe, AZ (US)

( * ) Notice: Subject to any disclaimer, the term of this patent is extended or adjusted under 35 U.S.C. 154(b) by 0 days.

(21) Appl. No.: 10/356,865

(22) Filed: Feb. 3, 2003

(65) Prior Publication Data
US 2003/0113956 A1 Jun. 19, 2003

Related U.S. Application Data

(62) Division of application No. 09/804,886, filed on Mar. 13, 2001, now abandoned.

(51) Int. Cl.[7] .................................................. H01J 9/24
(52) U.S. Cl. ............................................................ 445/24
(58) Field of Search ................................ 445/24, 25, 50, 445/51; 313/500–512

(56) References Cited

U.S. PATENT DOCUMENTS

| | | | |
|---|---|---|---|
| 5,047,686 A | 9/1991 | Robertson | ................ 313/503 |
| 6,388,377 B1 | 5/2002 | Kobayashi et al. | ......... 313/505 |
| 6,403,237 B1 * | 6/2002 | Noguchi et al. | ............ 313/506 |

FOREIGN PATENT DOCUMENTS

| | | | |
|---|---|---|---|
| EP | 0 964 045 A1 | 12/1999 | ........... C09K/11/06 |
| EP | 0 986 112 A2 | 3/2000 | ........... H01L/51/20 |
| EP | 1 065 725 A2 | 1/2001 | ........... H01L/27/15 |
| WO | WO 0117319 A | 3/2001 | ........... H05B/33/10 |

* cited by examiner

Primary Examiner—Joseph Williams
(74) Attorney, Agent, or Firm—Baker Botts L.L.P.

(57) ABSTRACT

A display device consisting of a multi-color light emitting layer and method of depositing the multi-color light emitting layer over a glass substrate are provided. The display device consists of multiple light emitting materials deposited over a glass substrate in coplanar relationship to each other. The method provides depositing one light emitting polymer material over one portion of the glass substrate and depositing other light emitting polymer materials over other portions of the glass substrate, such that the multiple light emitting polymer materials are deposited in a coplanar relationship to each other. The light emitting polymer materials are deposited using flexographic mats, the relief portion of which have patterns corresponding to the respective portions of the glass substrate being covered by the light emitting polymer materials being deposited.

16 Claims, 5 Drawing Sheets

DISPLAY DEVICE FORMED OF A MULTI-COLOR LIGHT EMITTING MATERIAL AND METHOD OF MAKING SAME

CROSS-REFERENCE TO RELATED APPLICATION

This application is a Divisional Patent Application of commonly owned U.S. patent application Ser. No. 09/804,886, filed Mar. 13, 2001, entitled "Display Device Formed of a Multi-Color Light Emitting Material and Method of Making Same", by Joseph Hourigan Morrissy and Dan Jerry Schott, now abandoned.

FIELD OF THE INVENTION

The present invention relates generally to light emitting devices, and more particularly to a display device having multiple light emitting materials deposited in a coplanar relationship to each other and method for depositing multiple light emitting materials on selected areas of the image generating surface of an electro-luminescent or electro-phosphorescent display device.

BACKGROUND OF THE INVENTION

Organic Electro-luminescent and Electro-phosphorescent display devices are replacing traditional liquid crystal display devices (LCDs) in certain applications employing flat panel displays. These devices employ an organic layer of material, which emits light when current flows in the presence of a forward-bias voltage. The advantage of these devices is that unlike traditional LCDs, they are self-luminous, and thus do not require backlighting. This eliminates the need for cumbersome backlights, and thus results in a thinner, more compact display device. Electro-luminescent and Electro-phosphorescent display devices also have a wider viewing angle (up to 160 degrees), and may require less power to operate than traditional backlit LCD devices. Electro-luminescent and Electro-phosphorescent display devices are thus smaller, lighter and more efficient to use than traditional LCD devices.

The principle behind electro-luminescence is that photons are given off as electrons that are injected from a metal cathode recombine in the organic (luminescent) material with holes that are injected from an anode material. The photons are seen as light. The photons can be released from different energy states. The basic energy states being researched are the singlet, at which approximately only 25% of the maximum light is emitted, and the triplet, at which approximately 75% of the maximum light is emitted. Most of the research and development work has traditionally been done in obtaining light emission at the singlet level. Recently, however, a number of university researchers have investigated obtaining light emission at the triplet level. Ideally, obtaining light emissions from both levels would be possible, so as to achieve 100% efficiency.

There are two basic types of electro-luminescent devices. One is known as an OLED device, which stands for organic light emitting diode. OLEDs employ a small molecule system, which must be evaporated or sublimed. OLED cells comprise a stack of thin organic layers sandwiched between a transparent anode and a metallic cathode deposited on a transparent substrate. The organic layers typically comprise a hole-injection layer, a hole-transport layer, an emissive layer and an electron-transport layer. When an electric current is passed between the electrodes, the injected positive and negative charges recombine in the emissive layer to produce light (electroluminescence). The organic layers, anode and cathode are preferably selected to maximize the recombination process in the emissive layer, and thereby maximize the light output from the OLED.

The color of the light depends upon the particular type of organic material used. Different areas of the cell could have different types of organic material. The different color generating organic materials are deposited over the transparent substrate using masks. That is, separate masks are used for the deposition of red, green, and blue materials.

Polymer LEDs (PLEDs), or LEPs (light emitting polymers) as they are known, are another type of electroluminescence device. Unlike OLEDs, which use a small molecule system, LEPs use long chain polymers. Although the properties between OLEDs and LEPs are very similar, the manner in which these systems are deposited is quite different. The organic light emitting layers of OLED devices are deposited using a vacuum deposition technique and different color OLED materials can be deposited in a pattern on the glass by using a shadow mask. The polymer light emitting layers of LEPs, however, are commonly deposited in solution, by spin coating the solution onto the surface of the glass substrate. The coating is then baked dry. A drawback of the spin coating process is that only one layer (color) can be deposited. Multiple colors cannot be photo-patterned. This is because the organic solvents used in the photo-resist and the inorganic water or solvent-based developing solutions attack the organic/polymer materials.

Accordingly, a drawback of prior art LEPs is that their deposition technique cannot generate inexpensive, multiple spatial colors, e.g., area-color or full color without the use of a secondary color filter plate. In one such prior art device, a yellow emitter, is used. While the emission spectrum of such a polymer is very broad, it has not been able to generate the entire spectrum. It is possible to obtain green, yellow, orange, and red colors from a yellow emitter by the use of a color filter, however the color blue cannot be generated. Another reason the use of color filter plates is considered undesirable is that they decrease the brightness of the secondary colors by a large amount, generally in excess of 67%. To compensate for this requires additional current and voltage to be supplied to the display, which is undesirable because additional power is consumed and the display components are placed under greater stress.

Ink-jet printing techniques have been proposed as a solution to generate high resolution, full-color displays. The drawback of this approach, however, is that the use of ink-jet printing to produce relatively large areas for each color is a relatively slow and expensive process and control of the location and amount of material has been difficult.

SUMMARY OF THE INVENTION

The present invention is directed to overcoming, or at least minimizing the drawbacks of the prior art display devices.

In one embodiment of the present invention, a method of depositing a multi-color light emitting layer over a transparent substrate used in a display device is provided. First, a first transparent conductive layer, preferably indium tin oxide, is deposited over the transparent substrate. This layer forms the anode of the emitting device. Next, a hole transport layer, preferably PEDT—PSS (polyethylene dioxythiophene—polystyrene sulphonate), is deposited over the conductive layer. This layer facilitates the communication of positive charge (electron deprived atoms) to the light emitting layer.

Next, one organic light emitting material, preferably a polymer, is deposited over one portion of the hole transport layer and another organic light emitting material, preferably another polymer, is deposited over another portion of the hole transport layer, such that the two organic light emitting materials are deposited in a coplanar relationship to each other. In other embodiments of the present invention, one or more additional organic light emitting materials are deposited over yet another portion or portions of the hole transport layer. The organic light emitting materials are preferably deposited using flexographic mats, the relief portion of which have patterns corresponding to the respective portions of the hole transport layer being covered by the organic light emitting materials being deposited. Each organic light emitting material is heated after it is deposited. The step of heating the organic light emitting materials is preferably performed in a convection oven at approximately 100 to 150 degrees Centigrade for approximately 30–90 minutes.

Next, an electron transport layer, preferably cyano PPV [poly-(cyano tere-phthalylidene)], is deposited over both light emitting materials. The electron transport layer is a layer that facilitates the communication of negative charge (electrons) to the light emitting layer. Finally, a second conductive layer, preferably a very thin layer of lithium fluoride followed by a thicker layer of aluminum, is deposited over the electron transport layer. This layer forms the cathode of the light emitting device.

All of the layers, except the multi-color light emitting layer, are preferably deposited using a flexographic printing process or a spin coating process or a vacuum deposition process or other deposition technique known in the art. Although one deposition technique is preferred to be used to deposit all of these layers, a hybrid of techniques may be used, i.e., one technique may be used to deposit one layer and another technique may be used to deposit another layer.

In another embodiment of the present invention, a display device comprising a multi-color light emitting layer deposited over a transparent substrate is provided. The multi-color light emitting layer according to the present invention includes at least two organic light emitting materials deposited in a coplanar relationship to each other. Each of at the least two light emitting materials is preferably a polymer. In other embodiments of the present invention, one or more additional organic light emitting materials are deposited in a coplanar relationship to the at least two organic light emitting materials and each other.

BRIEF DESCRIPTION OF THE DRAWINGS

Other objects and advantages of the invention will become apparent upon reading the following detailed description and upon reference to the drawings in which.

DETAILED DESCRIPTION OF THE PREFERRED EMBODIMENTS

Figure 1:
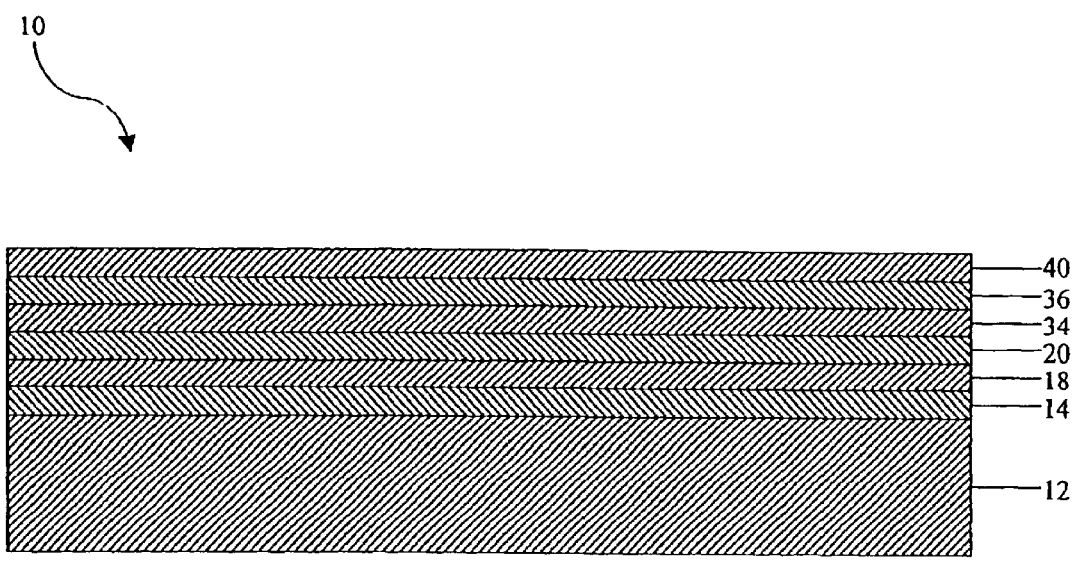
FIG. 1 is a cross sectional view of a multi-color display device according to the present invention.

Turning to the drawings, the preferred embodiments of the present invention will now be described. Referring initially to FIG. 1, the display device according to the present invention is indicated generally by reference numeral 10. At the base of the display device 10 is a glass substrate 12, which is preferably formed of passivated soda-lime glass preferably to a thickness of 0.4 to 1.1 mm. As those of ordinary skill in the art will appreciate, other transparent materials, including borosilicate and other glasses or amorphous or polysilicon structures, could be used as the base layer. In addition, non-transparent materials, including a processed silicon substrate, could also be used as the base layer provided that the cathode layer was a transparent material.

Figure 2:
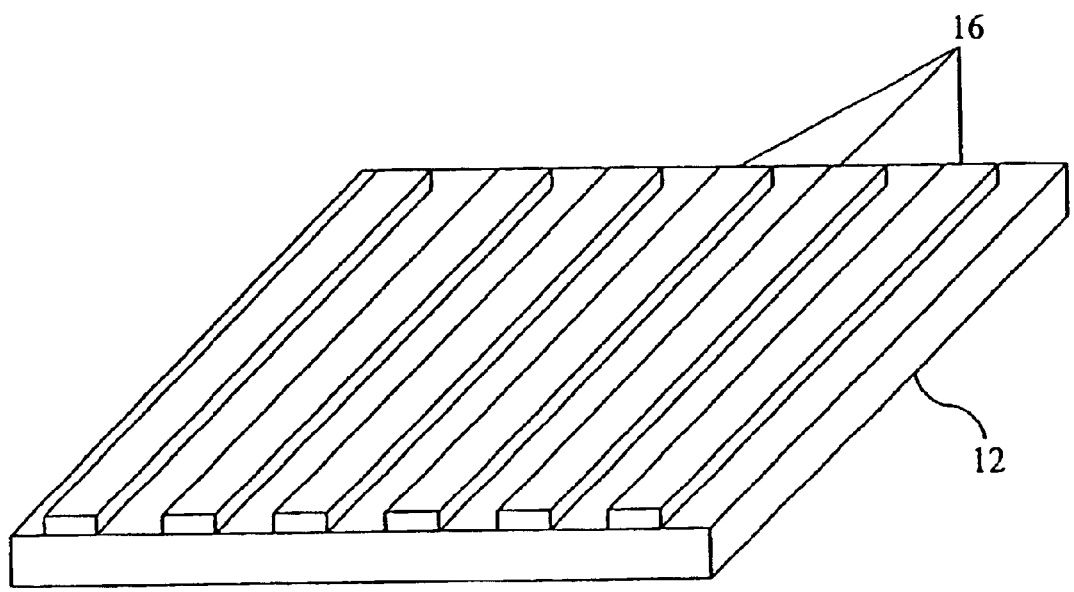
FIG. 2 is a planar view of a partial section of the multi-color display device shown in FIG. 1 illustrating the anode of said device, which is arranged in an array of parallel strips.

A conductive layer 14, preferably formed of indium tin oxide (ITO), is deposited over the glass substrate 12. The conductive layer 14 may be formed by vacuum depositing the ITO onto the surface of the glass substrate 12. As those of ordinary skill in the art will appreciate, other deposition techniques well known in the art may be employed. Once the ITO material is deposited over the entire surface of the glass substrate 12, the conductive layer 14 is then etched, using, for example, a photo-etch process, to form an array of parallel strips, which form anodes 16, as shown in FIG. 2. The conductive layer 14 is preferably 2000–3000 Angstroms in thickness in order to minimize the resistance of the anode conductors. As those of ordinary skill in the art will appreciate, other transparent conductive materials could be used to form the anode layer 14.

Next, a hole transport layer 18 is deposited over the conductive anode layer 14, as shown in FIG. 1. The hole transport layer 18 is preferably formed of PEDT—PSS, and is deposited to a thickness of approximately 200 to 400 angstroms. The hole transport layer 18 is preferably deposited over the entire structure by spin coating a solution of PEDT—PSS onto the surface of conductive layer 14. However, as pointed out above, vacuum deposition or other deposition techniques known in the art may also be used.

Next, a multi-color light emitting layer 20 is deposited over the hole transport layer 18. The multi-color light emitting layer 20 is preferably formed as follows. First, an organic light emitting material 22 (shown in FIG. 3), which when activated emits a particular color, is deposited over a portion of the hole transport layer 18. Preferably, the organic light emitting material 22 is a polymer selected from the group consisting of doped-poly-phenylene vinylene (doped-PPV), poly-arylenes or poly-fluorenes. Although, as those of ordinary skill in the art will appreciate, other polymer or non-polymer organic materials may be used. The organic light emitting material 22 is preferably deposited over a portion of the hole transport layer 18 using a flexographic mat 24, which contains relief areas 26 corresponding to the region over the hole transport layer 18 where it is desired to deposit the organic light emitting material 22, as shown in FIG. 4. In particular, the organic light-emitting material 22 is applied to the flexographic mat 24, which in turn, is pressed over the surface of the hole transport layer 18.

After the organic light emitting material 22 is deposited over the desired portion of the hole transport layer 18, the material is heated. More specifically, the entire structure is placed in a convection oven and heated to 100 to 150 degrees Centigrade for a period of 30–90 minutes so as to dry bake the organic light-emitting material 22 onto the surface of the hole transport layer 18.

Next, another organic light emitting material 28 (shown in FIG. 3) is deposited over another portion of the hole transport layer 18 different from the portion covered by the first organic light-emitting material 22. The organic light emitting material 28 emits a different color than the organic light-emitting material 22. Preferably, the organic light emitting material 28 is also a polymer selected from the group consisting of doped-PPV, poly-arylenes or poly-fluorenes. Again, however, as those of ordinary skill in the art will appreciate, other polymer or non-polymer organic materials may be used. The organic light emitting material 28 is preferably deposited over a portion of the hole transport layer 18 using a different flexographic mat 30, which contains a different relief area 32 corresponding to the region over the hole transport layer 18 where it is desired to deposit the organic light emitting material 28, as shown in FIG. 4. The organic light emitting material 28 is applied to the flexographic mat 30, which in turn, is pressed over the surface of the hole transport layer 18.

After the organic light emitting material 28 is deposited over the desired portion of the hole transport layer 18, the material is heated. More specifically, the entire structure is placed in a convection oven and heated to 100 to 150 degrees Centigrade for a period of 30–90 minutes so as to dry bake the organic light emitting material 28 onto the surface of the hole transport layer 18.

Figure 3:
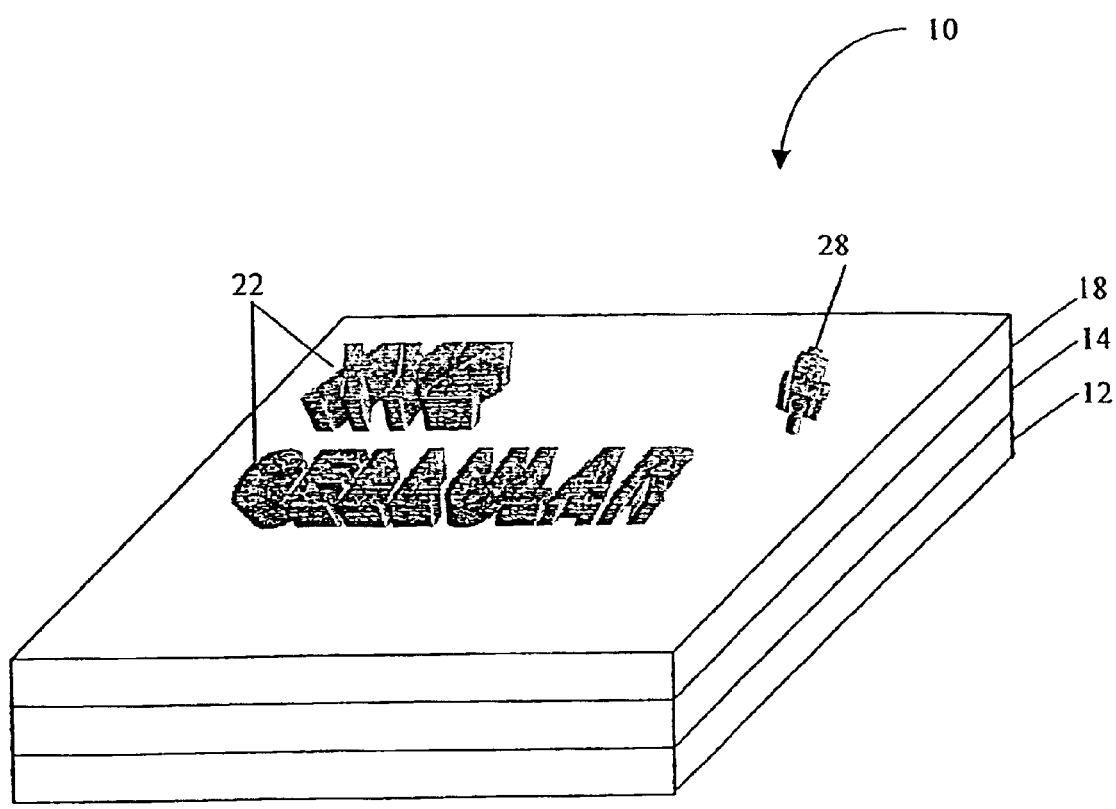
FIG. 3 is a planar view of a partial section of the multi-color display device shown in FIG. 1 illustrating a multi-color, light emitting material layer.
Figure 4:
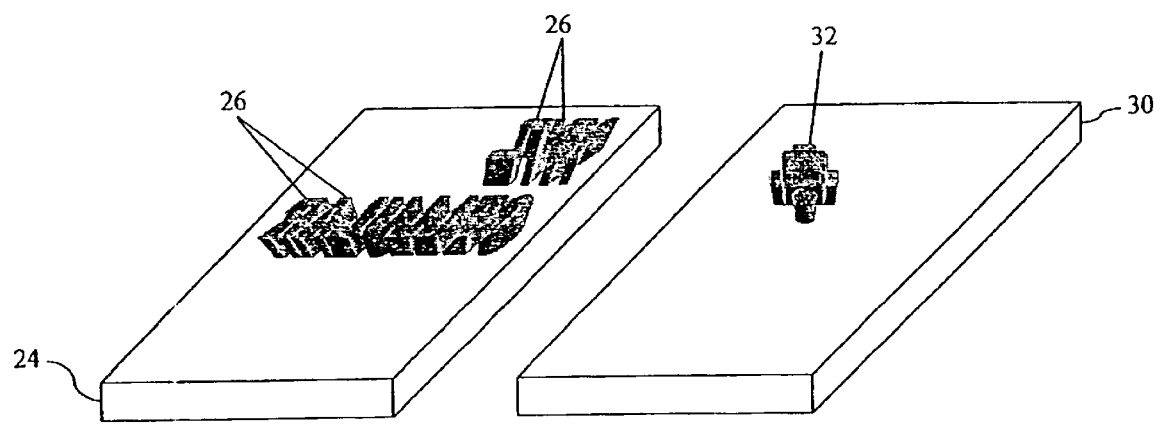
FIG. 4 is a planar view of two flexographic mats used in depositing the multi-color light emitting material layer shown in FIG. 3.

Although only two light emitting materials are shown in FIG. 3, as those of ordinary skill in the art will appreciate, other light-emitting materials may be used to cover different portions of the display device. 10. Regardless of how many different light emitting materials are ultimately deposited, all such materials are deposited so as to be in coplanar relationship with one another, as shown in FIG. 3. The result is a single multi-color light emitting layer 20, which is preferably 200 to 400 angstroms in thickness.

Next, an electron transport layer 34 is deposited over the multi-color light emitting layer 20, as shown in FIG. 1. The electron transport layer 34 is preferably formed of a cyano-PPV and is deposited to a thickness of approximately 200 to 400 angstroms. The electron transport layer 34 is preferably deposited over the entire structure by spin coating a solution of poly(cyano tere-phthalylidene) onto the surface of the multi-color light emitting layer 20. However, as pointed out above vacuum deposition, or other deposition techniques known in the art may also be used.

Figure 5:
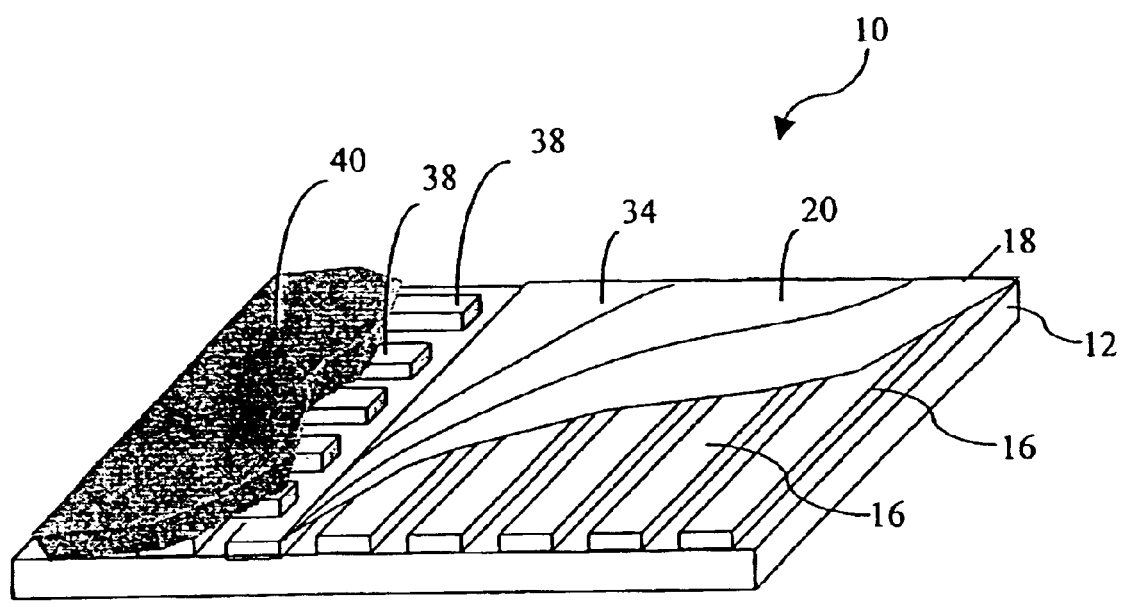
FIG. 5 is a planar view of a partial section of the multi-color display device shown in FIG. 1 illustrating the cathode of said device, which is also arranged in an array of parallel strips, disposed over the anode of said device.

Next, a conductive metal layer 36 is deposited over the electron transport layer 34, as shown in FIG. 1. The conductive metal layer 36 is preferably formed of a very thin film of lithium fluoride (0.5–1.0 nm) overcoated with a thick film (approx. 200 nm) of aluminum, although other similar materials can be used. The metal conductive layer 36 is preferably deposited to a thickness of approximately 2000 angstroms. The conductive metal layer 36 is preferably deposited over the entire structure by vacuum deposition onto the surface of the electron transport layer 34, however, as pointed out above spin coating a solution of lithium fluoride or aluminum, or other deposition techniques known in the art may be used. Once conductive metal layer 36 is deposited over the entire surface of the electron transport layer 34, the conductive metal layer 36 is then etched, using, for example, a plasma or a photo-etch process, to form an array of parallel strips, which form cathodes 38, as shown in FIG. 5. Alternatively, the cathode may be vacuum deposited via a patterned shadow mask. Another alternative would be to deposit onto the anode structure an array of separator ribs that would define the gaps between cathodes.

The array of cathodes 38 is disposed in a different plane than the array of anodes 16. The array of cathodes 38 are also disposed in perpendicular relationship to the array of anodes 16, so as to form a matrix or grid. The matrix or grid formed by said array of anodes and array of cathodes in turn forms a matrix of pixels, having for example an approximate size of 300 microns by 300 microns. A particular pixel is activated by activating the anode row and cathode column that defines the pixel. What is displayed on the display screen is a dot or microsquare of the color given off by the particular light emitting material disposed between the portion of the anode and cathode defining the pixel. Anode rows and cathode columns are activated (selected) using addressing techniques well known in the art.

Finally, a layer of protective material 40, preferably formed of a metal can containing an oxygen getter, is deposited over the conductive metal layer 36 to a thickness of approximately 0.2 mm. The layer of protective material 40 is preferably attached to the coated glass substrate by using an adhesive. However, other protective layers may also be used such as a polymer multi-layer or an inorganic hard-coat or a glass sheet.

As those of ordinary skill in the art will appreciate, the present invention is susceptible to various modifications and alternative forms. For example, in one alternate embodiment, an inverted structure is used where the cathode is the first layer deposited on the substrate and the anode is the final layer. Furthermore, additional process steps may be used in constructing a completed display device in accordance with the present invention. It should be understood also that the description herein of specific embodiments is not intended to limit the invention to the particular forms disclosed, but on the contrary, the intention is to cover all modifications, equivalents, and alternatives falling within the spirit and scope of the invention as defined by the appended claims.

What is claimed is:

1. A method of depositing a multi-color light emitting layer over a transparent substrate used in a display device, comprising the steps of:

(a) depositing a first conductive layer over the transparent substrate;

(b) depositing a hole transport layer over the conductive layer;

(c) depositing a first light emitting material over one portion of the hole transport layer using a flexographic mat, the relief portion of which has a pattern corresponding to the portion of the hole transport layer being covered by the first light emitting material being deposited;

(d) depositing a second light emitting material over another portion of the hole transport layer using a flexographic mat, the relief portion of which has a pattern corresponding to the portion of the hole transport layer being covered by the second light emitting material being deposited; and (e) depositing a second conductive layer over the first and second light emitting materials.

2. The method of depositing a multi-color light emitting layer according to claim 1, further comprising the step of heating the first light emitting material after that layer is deposited and before the second light emitting material is deposited.

3. The method of depositing a multi-color light emitting layer according to claim 2, further comprising the step of heating the second light emitting material after it is deposited and before the second conductive layer is deposited.

4. The method of depositing a multi-color light emitting layer according to claim 3, wherein the steps of heating the first and second light-emitting materials comprises heating the light emitting materials in a convection oven at approximately 100 to 150 degrees Centigrade for approximately 30–90 minutes.

5. The method of depositing a multi-color light emitting layer according to claim 1, wherein the step of depositing a first conductive layer over the transparent substrate comprises the step of depositing indium tin oxide over the transparent substrate.

6. The method of depositing a multi-color light emitting layer according to claim 1, wherein the step of depositing the hole transport layer comprises the step of depositing PEDT-PSS over the first conductive layer.

7. The method of depositing a multi-color light emitting layer according to claim 1, further comprising the step of depositing an electron transport layer comprised of poly (cyano tere-phthalylidene) between the layer of light emitting materials and the second conductive layer.

8. The method of depositing a multi-color light emitting layer according to claim 1, wherein the step of depositing the second conductive layer over the layer of light emitting materials comprises the step of depositing lithium fluoride and aluminum over the layer of light emitting materials.

9. The method of depositing a multi-color light emitting layer according to claim 1, further comprising the step of depositing one or more additional light emitting materials over yet another portion or portions of the hole transport layer.

10. The method of depositing a multi-color light emitting layer according to claim 1, wherein step (c) comprises depositing a polymer selected from the group consisting of PPV, poly-arylenes and poly-fluorenes over the one portion of the hole transport layer and step (d) comprises depositing a different polymer selected from the group consisting of PPV, poly-arylenes or poly-fluorenes over the another portion of the hole transport layer.

11. The method of depositing a multi-color light emitting layer according to claim 1, wherein the step of depositing the first conductive layer over the transparent substrate comprises the step of depositing lithium fluoride and aluminum over the transparent substrate and the step of depositing the second conductive layer over the layer of light emitting materials comprises the step of depositing indium tin oxide over the layer of light emitting materials.

12. A method of depositing a multi-color light emitting layer over a transparent substrate used in a display device, comprising the steps of:
(a) depositing a first light emitting material over one portion of the transparent substrate using a flexographic mat, the relief portion of which has a pattern corresponding to the portion of the substrate being covered by the first light emitting material being deposited; and
(b) depositing a second light emitting material over another portion of the transparent substrate using a flexographic mat, the relief portion of which has a pattern corresponding to the portion of the substrate being covered by the second light emitting material being deposited.

13. The method of depositing a multi-color light emitting layer according to claim 12, further comprising the step of heating the first light emitting material after that layer is deposited and before the second light emitting material is deposited.

14. The method of depositing a multi-color light emitting layer according to claim 13, wherein the steps of heating the light emitting materials comprises heating the organic light emitting materials in a convection oven at approximately 100 to 150 degrees Centigrade for approximately 30–90 minutes.

15. The method of depositing a multi-color light emitting layer according to claim 12, further comprising the step of depositing one or more additional light emitting materials over yet another portion or portions of the transparent substrate.

16. The method of depositing a multi-color light emitting layer according to claim 12, wherein step (a) comprises depositing a polymer selected from the group consisting of PPV, poly-arylenes and poly-fluorenes over the one portion of the transparent substrate and step (b) comprises depositing a different polymer selected from the group consisting of PPV, poly-arylenes or poly-fluorenes over the another portion of the hole transparent substrate.

* * * * *